United States Patent

Henkelmann et al.

(10) Patent No.: US 6,740,726 B2
(45) Date of Patent: May 25, 2004

(54) POLYISOCYANATES AS COATING COMPONENTS FOR COATING MEANS RICH IN SOLIDS

(75) Inventors: Jochem Henkelmann, Mannheim (DE); Heiko Maas, Mannheim (DE); Gerhard Schulz, Ludwigshafen (DE); Armin Stamm, Mainz (DE); Heinz-Peter Rink, Münster (DE); Werner-Alfons Jung, Ascheberg (DE); Peter Schwab, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 12 days.

(21) Appl. No.: 10/203,818

(22) PCT Filed: Feb. 16, 2001

(86) PCT No.: PCT/EP01/01784
§ 371 (c)(1),
(2), (4) Date: Aug. 14, 2002

(87) PCT Pub. No.: WO01/60885
PCT Pub. Date: Aug. 23, 2001

(65) Prior Publication Data
US 2003/0023114 A1 Jan. 30, 2003

(30) Foreign Application Priority Data

Feb. 16, 2000 (DE) .......... 100 06 901
Feb. 16, 2000 (DE) .......... 100 06 902

(51) Int. Cl.$^7$ .............................. C08G 18/72
(52) U.S. Cl. .......... 528/67; 528/45; 560/330; 560/347; 252/182.2; 252/182.21; 525/123
(58) Field of Search ............. 528/45, 67; 560/330, 560/347; 252/182.2, 182.21; 525/123

(56) References Cited

U.S. PATENT DOCUMENTS

| 5,633,396 | A | 5/1997 | Bischof |
| 5,716,678 | A | 2/1998 | Roeckrath |
| 5,759,631 | A | 6/1998 | Rink |
| 6,013,739 | A | 1/2000 | Rink |
| 6,100,326 | A | 8/2000 | Richter |
| 6,353,141 | B1 * | 3/2002 | Zeller et al. |

FOREIGN PATENT DOCUMENTS

| DE | 43 10414 | 10/1994 |
| DE | 44 07409 | 9/1995 |
| DE | 44 07415 | 9/1995 |
| EP | 013 493 | 7/1980 |
| EP | 749 958 | 12/1996 |
| EP | 928 799 | 7/1999 |

* cited by examiner

Primary Examiner—Rachel Gorr
(74) Attorney, Agent, or Firm—Keil & Weinkauf

(57) ABSTRACT

A description is given of polyisocyanates of the formula I

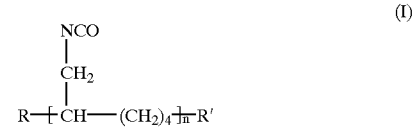

in which
R and R' are identical or different and are alkyl groups having 1–4 carbon atoms and
n is on average from 1.5 to 5
and also of a process for preparing these polyisocyanates in which a polyamine of the formula II

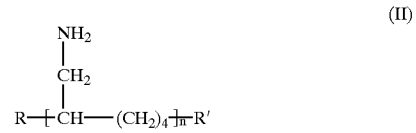

in which R, R', and n are as defined above, is reacted with phosgene. The new polyisocyanates are suitable for producing crosslinked polyurethanes from reaction mixtures with low solvent content and for producing coating compositions or adhesives. Also described are the coating compositions and adhesives, and their use.

9 Claims, No Drawings

POLYISOCYANATES AS COATING COMPONENTS FOR COATING MEANS RICH IN SOLIDS

The invention relates to aliphatic polyisocyanates, to a process for preparing them, to coating compositions and adhesives comprising the aliphatic polyisocyanates, and to the use of the polyisocyanates, coating compositions, and adhesives.

Aliphatic polyisocyanates, i.e., isocyanates having more than one, preferably more than two, isocyanate groups per molecule, are known and are used, inter alia, as crosslinkers for preparing polyurethanes suitable as binders for paints. Since reducing the solvent content of paints is an objective with the aim of reducing emissions, it is necessary to have paint constituents of low viscosity in order to maintain a viscosity which is sufficiently low for the application of the paint. Commercial polyisocyanates which meet this condition are generally prepared by oligomerizing difunctional isocyanates, hexamethylene diisocyanate for example. In the course of this preparation, however, some of the isocyanate groups present originally are reacted and are lost to the subsequent crosslinking reaction. Moreover, this preparation process requires two steps to the polyfunctional isocyanate having three or more NCO groups.

Other polyfunctional isocyanates, an example being nonane triisocyanate, are prepared directly from the corresponding polyfunctional amines. Only a few such polyfunctional amines, however, are available on the industrial scale.

Paint systems known at present, such as clearcoats or topcoats, surfacers and primers, or underbody protection compositions for motor vehicles, have the disadvantage that their solids contents cannot be increased ad infinitum. Paint systems of this kind are known from DE 44 07 415, DE 44 07 409 or DE 43 10 414. Raising the solids content of paints in order to reduce solvent emission is, however, a stated aim of the paint industry. The same applies accordingly to adhesives and sealing compounds.

It is an object of the invention to provide new aliphatic polyisocyanates which with two or more NCO groups per molecule are of low viscosity and whose molecule size and number of NCO groups may be varied as desired, and to provide a process for preparing them that requires no further reaction after the NCO groups have been introduced.

It is a further object of the present invention to provide coating compositions and adhesives which as compared with their prior art counterparts have an increased solids content and permit low-emission formulations.

We have found that these objects are achieved firstly by polyisocyanates of the formula I

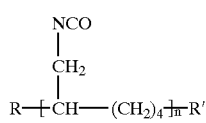   (I)

in which
  R and R' are identical or different alkyl groups having 1–4 carbon atoms and
  n is on average from 1.5 to 5,
and secondly by a coating composition or adhesive comprising
  a) polyisocyanates of the formula I, which may be present in blocked form, as crosslinkers,
  b) if desired, further crosslinkers, and
  c) isocyanate-reactive polymers, oligomers and/or low molecular mass compounds, as binders.

Polyisocyanates of the formula I are therefore compounds containing on average from 1.5 to 5 NCO groups, i.e., essentially those representatives which may be referred to as oligomers. The polyisocyanates of the formula I are frequently in the form of homolog mixtures which include representatives where n=1 to about n=10 and are preferably composed essentially of these representatives.

The invention further proposes a process for preparing polyisocyanates of the formula I which comprises reacting a polyamine of the formula II

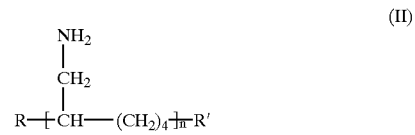   (II)

in which R, R', and n are as defined above with phosgene, preferably in excess.

The polyamines may be reacted in one stage at elevated temperature (generally from 120 to 170° C.) or, with particular advantage, in two stages, first at relatively low temperatures in the range from −15 to +10° C. (cold phosgenation) and then with an increase to from 130 to 165° C. (hot phosgenation). Particularly good yields are achieved if the amine is first converted to the hydrochloride and then subjected to cold phosgenation at from 50 to 70° C. and to hot phosgenation at from 120 to 170° C. Phosgene is generally used in an excess of from 10 to 30 mol %, so that, normally, substantially all of the primary amino groups are converted to isocyanate groups. It is, however, also possible to use larger phosgene excesses. The excess phosgene can be removed with ease and recycled to the synthesis.

The reaction may be conducted without the addition of inert solvents. In general, however, it is of advantage to operate in an aprotic solvent such as a halogenated, especially chlorinated, aromatic, preferably mononuclear, hydrocarbon such as dichlorobenzene.

The compounds of the formula II are known and are described, for example, in DE-A 196 54 167. They are preferably obtained by catalyzed metathesis reactions of hydrocarbon mixtures comprising cyclopentene, e.g., petroleum fractions, subsequent hydroformylation of the reaction products, and reaction thereafter with ammonia in the presence of hydrogen and a hydrogenation catalyst.

The polyisocyanates obtained are distinguished by particularly low viscosities, which are generally below 400 mPas. They are therefore outstandingly suitable for preparing low-solvent paint base material mixtures.

The present invention also provides for the use of the polyisocyanates of the formula I to prepare coating compositions and adhesives.

The average functionality of the isocyanates used in accordance with the invention is preferably from 1.5 to 5.0 and with particular preference from 1.5 to 3.5.

The polyisocyanates of the formula I may be used as sole crosslinkers or in blends with further crosslinkers. Examples of suitable further crosslinkers are amino resins, compounds or resins containing siloxane groups, compounds or resins containing anhydride groups, polyisocyanates and/or alkoxycarbonylaminotriazines.

The further crosslinkers preferably comprise or consist of other polyisocyanates, different than the polyisocyanates of the formula I. In principle it is possible to use all polyisocyanates that are common in the paints field. Preferred polyisocyanates are those whose isocyanate groups are attached to aliphatic or cycloaliphatic radicals. Examples are tetramethylene diisocyanate, hexamethylene diisocyanate, isophorone diisocyanate, trimethylhexamethylene diisocyanate, dicyclohexylmethane diisocyanate, 1,3-bis(2-isocyanatoprop-2-yl)benzene (TMXDI), 1,4- and 1,3-bis (isocyanatomethyl)cyclohexane, et cetera, and adducts of these polyisocyanates with polyols, and polyisocyanates derived from these polyisocyanates and containing isocyanurate groups and/or biureth groups.

The polyisocyanates of the formula I and the polyisocyanates used as further crosslinkers may be blocked or nonblocked.

Through the choice of the further crosslinkers and also through the use of the polyisocyanates in blocked or nonblocked form it is possible to configure the coating compositions and adhesives of the invention as one-component or two-component systems.

Blocked isocyanates may be employed in both one-component and two-component systems; preferably, they are employed in one-component systems. A general description of the preparation of suitable blocked isocyanates is given, for example, in DE-A 198 09 643. Blocked isocyanates preferably contain both isocyanate groups blocked with a first blocking agent and isocyanate groups blocked with a second blocking agent, the first blocking agent being a dialkyl malonate or a mixture of dialkyl malonates, preferably dialkyl malonates having 1–6 carbon atoms, and the second blocking agent preferably being an alkyl acetoacetate having 1–6 carbon atoms in the alkyl radical or a ketoxime, such as ethyl acetoacetate or methyl ethyl ketoxime. The ratio between the isocyanate groups blocked with the first blocking agent and those blocked with the second blocking agent is preferably between 8.0:2.0 and 6.0:4.0, suitable blocked polyisocyanates being obtainable by reacting the polyisocyanates with a mixture of the first and the second blocking agent or by mixing isocyanates blocked with the first blocking agent with polyisocyanates blocked with the second blocking agent, in the appropriate proportions. Suitable blocked polyisocyanates are also obtained by reacting some, preferably 70%, of the isocyanate groups of the polyisocyanate with a mixture of the first and second blocking agents and then reacting the remaining isocyanate groups with a hydroxyl-containing compound.

In the one-component systems, the polyisocyanates in blocked form may additionally be used as a blend with amino resins.

The coating compositions and adhesives of the invention may be two-component systems. In this case the coating composition or adhesive has a second component comprising as crosslinker a nonblocked polyisocyanate which, if desired, is dissolved in an organic solvent. Additionally, blocked polyisocyanates may be present in the second component. The nonblocked polyisocyanates comprise nonblocked isocyanates of the formula I used in accordance with the invention and, if desired, where further crosslinkers are present, in the desired further nonblocked organic polyisocyanates having free isocyanate groups attached to aliphatic, cyclo-aliphatic, araliphatic and/or aromatic moieties. Examples of further polyisocyanates are polyurethane prepolymers containing isocyanate groups, which can be prepared by reacting polyols with an excess of polyisocyanates and which are preferably of low viscosity. It is also possible, as further polyiso-cyanates, to use polyisocyanates containing isocyanurate groups, biureth groups, allophanate groups, urethane groups, urea groups, urethdione groups and/or iminooxadiazinedione groups. Polyisocyanates of this kind are likewise described in DE-A 198 09 643.

As further crosslinkers, moreover, use may be made of aliphatic triisocyanates such as 1,8-diisocyanato-4-isocyanatomethyloctane, 1,7-diisocyanato-4-isocyanatomethylheptane and/or tris(alkoxycarbonylamino) triazine.

In the overall crosslinker, the polyisocyanates of the formula I are generally present in fractions of from 5 to 100% by weight, preferably from 10 to 80% by weight, with particular preference from 20 to 70% by weight, i.e., based on the sum of the polyisocyanates of the formula I and of the further crosslinkers. It is also possible for the polyisocyanates of the formula I to be converted into, and used as, isocyanate-functional derivatives urethanes, allophanates, isocyanurates, etc., or mixtures thereof.

The coating compositions and adhesives of the invention comprise isocyanate-reactive polymers, oligomers and/or low molecular mass compounds as binder component. Suitable compounds include all hydroxy- and amino-functional, and also other isocyanate-reactive, polymers, oligomers, and low molecular mass compounds. The binder component preferably comprises hydroxy-functional polymers, oligomers and/or low molecular mass compounds, and with particular preference it consists of these. Hydroxy-functional polymers and/or oligomers are preferably selected from the group consisting of hydroxy-functional polyacrylates, polyesters, polyurethanes, acrylated polyurethanes, acrylated polyesters, polylactones, polycarbonates, polyethers, and (meth)acrylatediols. Preference is given to using polyacrylates, polyesters and/or polyurethanes, especially polyacrylates and/or polyesters. Suitable polyacrylates, polyestets, and poly-urethanes are described in DE-A 198 09 643.

Examples of suitable isocyanate-reactive compounds of low molecular mass are the branched, cyclic and/or acyclic $C_9$–$C_{16}$ alkanes which are described in DE-A 198 09 643 and are functionalized with at least two hydroxyl or thiol groups or with at least one hydroxyl and at least one thiol group. Of these, $C_9$–$C_{16}$ alkanepolyols are preferred. Particular preference is given to the positionally isomeric dialkyloctanediols, particularly diethyloctanediol, especially 2,4-diethyloctane-1,5-diol. These isocyanate-reactive compounds of low molecular mass may be present in the binder component, for example, in fractions of from 0.5 to 25% by weight, based on the overall amount of the binder.

The coating composition of the invention may further comprise UV absorbers, free-radical scavengers, crosslinking catalysts, rheological aids, pot life extenders, and further customary additives such as slip additives, polymerization inhibitors, flatting agents, defoamers, leveling agents, and film formation auxiliaries, e.g., cellulose derivatives, or other additives commonly used in basecoat materials. Suitable crosslinking catalysts include, in particular, organometallic compounds, preferably tin and/or organobismuth compounds. Tertiary amines are also suitable. Examples of pot life extender additives include acetylacetone and tertiary alcohols such as tert-butanol. Pigments of any kind, examples being color pigments such as azo pigments, phthalocyanine pigments, carbonyl pigments, dioxazine pigments, titanium dioxide, pigment-grade carbon black, oxides of iron, of chromium and of cobalt, or effect pigments such as metal flake pigments, especially aluminum flake pigments and pearlescent pigments, may be used.

The coating compositions and adhesives of the invention are prepared in accordance with customary methods by combining the individual constituents and mixing them with stirring.

The coating composition or adhesive of the invention are preferably formulated as a nonaqueous solution or dispersion. For this purpose it is possible to use the organic solvents customary in preparing paints or adhesives.

The coating composition of the invention is used in particular to produce coated moldings or composite parts which comprise or consist of films, glass, wood, paint and/or metal, by applying the coating composition to the corresponding moldings and curing the resulting coating.

The coating composition of the invention is used preferably to produce single-coat or multicoat paint systems and with particular preference to produce topcoats. However, it may also be intended for producing a clearcoat to be applied over a basecoat film, an example being a clearcoat of a multicoat paint system produced by the wet-on-wet technique. Furthermore, it may be used as a primer, surfacer or underbody protectant. The plastics or other substrates may also be coated directly with the clearcoat or the topcoat.

The coating compositions can be used in both the OEM finishing and the refinishing of automobile bodies. Preferably, however, they are used in the OEM finishing area.

The present invention also provides for the use of the coating compositions of the invention in automotive OEM finishing and automotive refinish as a clearcoat, topcoat, surfacer, primer and/or underbody protectant.

The adhesive of the invention is used to produce bonded composite parts which consist of or comprise films, plastics, glass, wood, paper and/or metal by applying the adhesive to the surface or surfaces of a film or of a molding comprising or consisting of plastic, glass, wood, paper and/or metal that is or are to be bonded and/or to the surface of the part that is to be bonded thereto and, if desired, subjecting the bond to initial curing, after which the relevant surfaces to be bonded are brought into contact and then the adhesive is cured to completion.

Application takes place generally by means of customary methods, such as by spraying, knifecoating, dipping, or brushing, for example.

The present invention also provides for the use of the coating compositions or adhesives of the invention for coating and bonding surfaces of plastic, wood, glass, paper or metal.

The coating compositions or adhesives of the invention are cured preferably at temperatures from room temperature up to 180° C. Temperatures of from 60° C. to 180° C. are particularly preferred. In special embodiments of the coating compositions of the invention it is also possible to employ lower curing temperatures of from 60° C. to 160° C.

The examples which follow describe preferred embodiments of the invention. The isocyanate numbers specified therein are determined in accordance with DIN 16945 and 53185 by reacting the isocyanate with excess dibutylamine and back-titrating the excess with hydrochloric acid against bromophenol blue. The amine number is defined as mg KOH/g product. It is determined by weighing out about 1.0 g of test substance precisely, dissolving it in 50 ml of acetic acid and titrating the solution potentiographically against standard 0.1 molar trifluoromethanesulfonic acid solution in acetic acid. A description of the method can be found in Huber, Titrationen in nichtwäβrigen Lösungsmitteln, Akademische Verlagsgesellschaft, Frankfurt a. M., p. 130 ff. (1964) and in Gyenes, Titrationen in nichtwäβrigen Medien, Ferdinand Enke Verlag, Stuttgart, p. 488 ff. (1970).

EXAMPLE 1

A 1 l stirred glass flask with gas inlet pipe, cooled in a brine cooler of −10° C. and a dry ice cooler, was charged at from −10 to 0° C. with 130 g of phosgene. 400 g of polyfunctional amine corresponding to the formula II, with an amine number of 235.3, and a further 470 g of phosgene were added over the course of 5 hours. This was followed by stirring at from −10 to 0° C. for 1 hour. The reaction mixture was heated to 150–160° C. and a further 136 g of phosgene were introduced over the course of 7 hours. Nitrogen was then passed through the reaction mixture at 150° C. until all of the phosgene had been removed. This gave 437 g of a polyfunctional isocyanate having an isocyanate number of 12.7 g per 100 g.

EXAMPLE 2

The apparatus indicated in Example 1 was charged with 270 g of phosgene, dissolved in 600 g of o-dichlorobenzene, at −10–0° C., and 150 g of a polyamine with an amine number of 235.3 was added dropwise at from −10° C. to 0° C. over the course of 3 hours. The mixture was then heated to 140–145° C. and a further 32 g of phosgene were introduced over the course of 2 hours. After subsequent reaction for 3 hours, the remaining phosgene was removed with nitrogen. The solvent was distilled off over a bridge under 0.5 mbar at a bath temperature of 100° C. This gave 131 g of polyisocyanate having an isocyanate number of 13.8.

EXAMPLE 3

As described in Example 2, 100 g of polyamine having an amine number of 306 were added dropwise over the course of 2 hours at from −10 to 0° C. to a solution of 170 g of phosgene in 200 ml of o-dichlorobenzene in a stirred glass apparatus. Stirring was then continued at 0° C. for 4 hours, followed by heating to 135–140° C. A further 30 g of phosgene were introduced over the course of 2 hours. After 5 hours of subsequent reaction at 135–140° C., the reaction mixture was stripped phosgene-free with nitrogen and the solvent was distilled off as described in Example 2. This gave 110 g of a polyisocyanate having an isocyanate number of 21.9.

EXAMPLE 4

The apparatus described in Example 1 was charged at from −10 to 0° C. with 340 g of phosgene in solution in 400 ml of o-dichlorobenzene, and 200 g of polyamine with an amine number of 306 were added dropwise at the same temperature over the course of 4 hours. After 4 hours of subsequent reaction at 0–5° C., the mixture was heated to 140° C. and a further 60 g of phosgene were introduced over the course of 2 hours. After 3 hours of subsequent reaction at 140° C., the reaction mixture was stripped phosgene-free with nitrogen and the solvent was distilled off as described in Example 2. This gave 220 g of a polyisocyanate having an isocyanate number of 21.3.

EXAMPLE 5

An apparatus as described in Example 1 was charged with 100 g of polyamine (amine number 306) (in 200 ml of o-dichlorobenzene) and hydrogen chloride was introduced at room temperature until saturation was reached. A white crystalline precipitate was obtained. The mixture was then heated to 60° C. and 170 g of phosgene were introduced over the course of 6 hours. The mixture was subsequently heated to 145° C. and a further 60 g of phosgene were introduced (duration: 2 hours). Thereafter the reaction mixture was worked up as described in Example 2. This gave 110 g of polyisocyanate having an isocyanate number of 24.7.

EXAMPLE 6

The following components were mixed homogeneously in the weight proportions stated:

- 62.1% by weight of a 57.4 strength by weight solution of a hydroxy-functional styrene polymer having an OH number of 155 and a Fox glass transition temperature of 66° C. in Solventnaphtha® (a commercial mixture of aromatic hydrocarbons having a boiling point range of from 160 to 185° C.)/methoxypropyl acetate/butyl acetate/butyl glycol acetate in a weight ratio of 33:5:6:3, as component A;
- 0.6% by weight of UV absorber based on triazine (Cyagard® 1164 L from Cytek) as component B;
- 0.9% by weight of HALS stabilizers (Tinuvin® 292 from Ciba Geigy) as component C;
- 0.2% by weight of polysilane-modified silicone additive (Byk® 310 from Byk) as component D;
- 6.6% by weight of solventnaphtha as component E;
- 4.4% by weight of butyl acetate as component F;
- 3.4% by weight of butyl diglycol acetate as component G;
- 14.3% by weight of a hexamethylene diisocyanate trimer (Desmodur® N3390 from Bayer) as component H;
- 19.9% by weight of a polyisocyanate of the formula I having a viscosity of 364 mPas and an NCO content of 9% by weight, a mass average $M_n$=879 and a weight average $M_w$=2630, prepared from cyclopentene oligomers, as component I.

Following application of the coating composition thus obtained, and drying of the paint film at 130° C. for a period of 30 minutes, coatings having good surface properties were obtained.

What is claimed is:

1. A polyisocyanate of the formula I

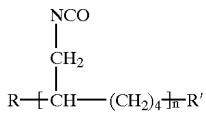

(I)

in which

R and R' are identical or different and are alkyl groups having 1–4, carbon atoms and n is on average from 1.5 to 5.

2. A polyisocyanate as claimed in claim 1, characterized in that it consists of a mixture of homologs with n=1 to n=10.

3. A polyisocyanate as claimed in claim 1, characterized in that it has a viscosity of below 400 mPas.

4. A process for preparing polyisocyanates of the formula I

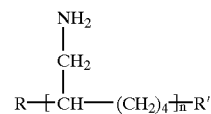

(II)

in which

R and R' are identical or different alkyl groups having 1–4 carbon atoms and n is on average from 1.5 to 5, characterized in that a polyamine of the formula II

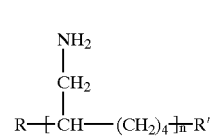

(II)

in which R, R' and n are as defined above is reacted with phosgene.

5. A coating composition or adhesive comprising
   a) polyisocyanates of the formula I as defined in 1, it being possible for the polyisocyanates to be in blocked form, as crosslinkers.
   b) if desired, further crosslinkers, and
   c) isocyanate-reactive polymers, oligomers and/or low molecular mass compounds, as binders.

6. A coating composition or adhesive as claimed in claim 5, characterized in that the fraction of the polyisocyanates of formula I in the overall crosslinker amount is from 5% by weight to 100% by weight.

7. A coating composition or adhesive as claimed in claim 5, characterized in that the further crosslinkers comprise blocked at nonblocked further polyisocyanate.

8. A coating composition or adhesive as claimed in claim 5 characterized in that the binder comprises hydroxy-functional polymers, oligomers and/or low molecular mass compounds.

9. A coating composition or adhesive as claimed in claim 8, characterized in that the binders are selected from the group consisting of hydroxy-functional polyacrylates, polyesters, polyurethanes, acrylated polyurethanes, acrylated polyesters, polylactones, polycarbonates, polyethers, (meth)acrylatediols, and $C_9$–$C_{14}$ alkanepolyols.

* * * * *

UNITED STATES PATENT AND TRADEMARK OFFICE
CERTIFICATE OF CORRECTION

PATENT NO.   : 6,740,726 B2
DATED        : May 25, 2004
INVENTOR(S)  : Henkelmann et al.

It is certified that error appears in the above-identified patent and that said Letters Patent is hereby corrected as shown below:

<u>Column 8,</u>
Line 50, "$C_9$-$C_{14}$ alkanepolyols" should read -- $C_9$-$C_{16}$ alkanepolyols --.

Signed and Sealed this

Twenty-ninth Day of March, 2005

JON W. DUDAS
*Director of the United States Patent and Trademark Office*